(12) United States Patent
Benchetrit

(10) Patent No.: US 6,878,137 B2
(45) Date of Patent: Apr. 12, 2005

(54) IMPLANTABLE DEVICE FOR INJECTING MEDICAL SUBSTANCES

(75) Inventor: Salomon Benchetrit, Caluire (FR)

(73) Assignee: Compagnie Europeenne d'etude et de Recherche de Dispositifs pour l'Implantation par Laparoscopie, Vienne (FR)

(*) Notice: Subject to any disclaimer, the term of this patent is extended or adjusted under 35 U.S.C. 154(b) by 0 days.

(21) Appl. No.: 10/203,223

(22) PCT Filed: Feb. 16, 2001

(86) PCT No.: PCT/FR01/00465
§ 371 (c)(1),
(2), (4) Date: Nov. 5, 2002

(87) PCT Pub. No.: WO01/60444
PCT Pub. Date: Aug. 23, 2001

(65) Prior Publication Data
US 2003/0135168 A1 Jul. 17, 2003

(30) Foreign Application Priority Data
Feb. 18, 2000 (FR) .......................... 00 02074

(51) Int. Cl.⁷ .................... A61M 31/00; A61M 37/00
(52) U.S. Cl. .............................................. 604/288.02
(58) Field of Search ................ 604/890.1, 891.1, 604/892.1, 48, 93.01, 288.01, 288.02, 288.03, 288.04

(56) References Cited

U.S. PATENT DOCUMENTS

| 4,762,517 A | * | 8/1988 | McIntyre et al. ........... 604/175 |
| 4,781,680 A | | 11/1988 | Redmond et al. ............. 604/93 |
| 4,840,615 A | | 6/1989 | Hancock et al. .............. 604/93 |
| 5,041,098 A | * | 8/1991 | Loiterman et al. .......... 604/175 |
| 5,137,529 A | | 8/1992 | Watson et al. ........... 604/891.1 |
| 5,460,612 A | | 10/1995 | Madore ....................... 604/116 |
| 5,476,460 A | * | 12/1995 | Montalvo ................ 604/891.1 |
| 6,213,973 B1 | * | 4/2001 | Eliasen et al. ........... 604/93.01 |
| 6,478,783 B1 | * | 11/2002 | Moorehead ............ 604/288.02 |

FOREIGN PATENT DOCUMENTS

WO 99/16501 4/1999 .......... A61M/39/02

* cited by examiner

Primary Examiner—Nicholas D. Lucchesi
Assistant Examiner—Mark K Han
(74) Attorney, Agent, or Firm—James W. Kayden; Thomas, Kayden, Horstemeyer & Risley, LLP

(57) ABSTRACT

An injection device (1) for injecting medical substances and designed to be implanted in a subcutaneous zone of the body of a patient. The device includes a hollow rigid housing (2) having an opening which is closed hermetically by a membrane (3) so as to define a chamber (12). A duct (4) is connected to the housing to connect the chamber to the outside of the device. The device also has a casing (15) of elastomer material which covers the housing, and the membrane forms an integral portion of the casing. The implantable device is suitable for performing chemotherapy treatment.

10 Claims, 2 Drawing Sheets

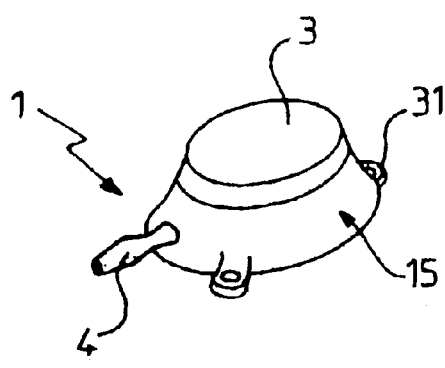
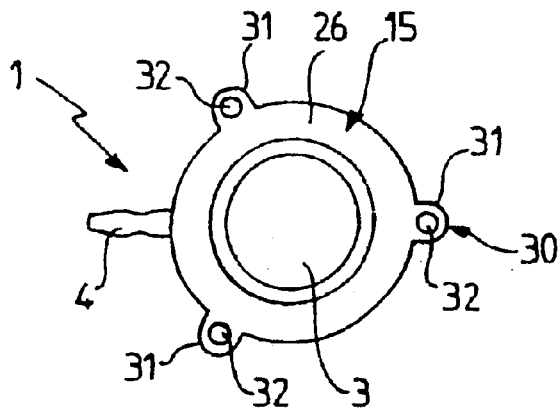
FIG. 1  FIG. 2
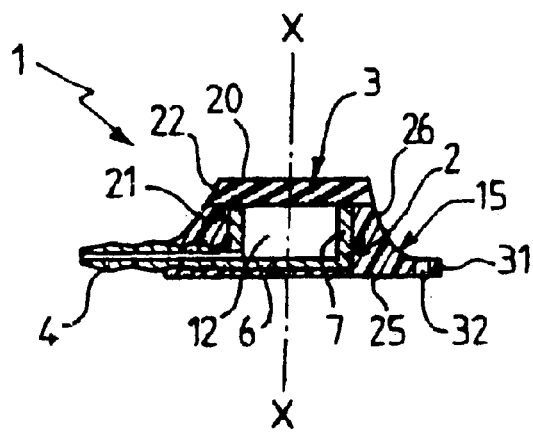
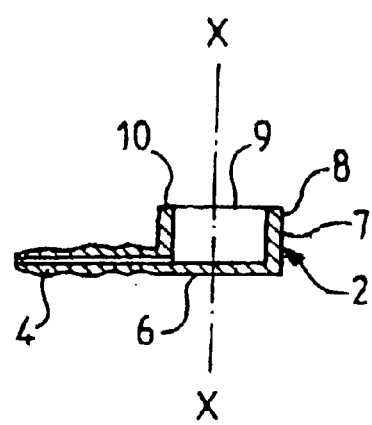
FIG. 3  FIG. 4

IMPLANTABLE DEVICE FOR INJECTING MEDICAL SUBSTANCES

CROSS REFERENCE TO RELATED APPLICATIONS

This application is a national phase of PCT/FR01/00465, filed Feb. 16, 2001, which claims priority to French Application Serial No. 00/02074, filed Feb. 18, 2000.

TECHNICAL FIELD

The present invention relates to the technical field of devices for injecting medical substances, which devices are designed to be implanted in a subcutaneous zone of the body of a patient in order to inject said substances into the body of the patient.

Such injection devices are also referred to implantable sites.

The present invention relates to an injection device of the type comprising a hollow rigid housing having a distal wall from which there extend side walls whose free ends define a proximal opening, a membrane which is situated over the free ends of the side walls in order to close the proximal opening in substantially hermetic manner, thereby defining a chamber, and a duct connected to the rigid housing and which connects the chamber to the outside of the injection device.

PRIOR ART

During injection, the membrane which is accessible through the skin of the patient is designed to be pierced by a needle so as to deliver a dose of medical substance into the body of the patient through the chamber and the duct. In order to prevent the needle from penetrating into the body of the patient when it is inserted into the chamber, the side walls and the distal wall of the housing are not suitable for being pierced.

Generally, the duct is connected to a catheter enabling the medical substance to be delivered directly into the region of the body that is to be treated. Such injection devices can remain in the body of the patient over long periods of time in order to avoid using repeated intravenous, intra-arterial, or indeed intraspinal injections during lengthy medical treatment, the injections being replaced merely with subcutaneous injections. This reduces the physiological and psychological trauma to which the patient is subjected.

Nevertheless, medical standards require the housing to be sufficiently rigid to ensure that, during injection, there is no risk of a needle reaching the patient's body after it has been pushed through the membrane. Consequently, presently-known injection devices still create trauma in the body of the patient because of their rigidity.

Furthermore, in presently-used implantable sites, the membrane is generally held in place on the free ends of the side walls of the rigid housing by any conventional mechanical locking means. Even if the membrane is initially locked in place so as to ensure that the chamber of the injection device is hermetically sealed, prolonged use of the device degrades such locking, and thus gives rise to risks of leakage or of the membrane becoming completely separated. The device then needs to be changed and replaced with a new device which means that new surgery is required, thus giving rise to considerable discomfort for the patient.

SUMMARY OF THE INVENTION

Consequently, the object of the invention is to propose a novel device for injecting medical substances that makes it possible to remedy the various drawbacks set out above, by providing a device which is not traumatic while eliminating any risk of leakage or of the membrane becoming separated, the device being simple in design and facilitating the injection operation in general.

Another object of the invention is to propose a novel injection device which facilitates insertion of the needle into the chamber of the housing so as to ensure that the user of the needle does not need to puncture the skin of the patient several times in order to locate the membrane. It is not always possible to locate the surface of the membrane accurately merely by palpating the skin of the patient. Thus, the proposed device makes it possible to reach the chamber in complete safety, even if the needle is inserted at an angle through the thickness of the membrane.

Another object of the invention is to provide a novel injection device which is particularly stable while using a small number of elements.

Another object of the invention is to propose a novel injection device which is easy to immobilize within the body of the patient.

The objects allocated to the invention are achieved by means of a novel device for injecting medical substances for implanting in a subcutaneous zone of the body of a patient in order to inject said substances into the body, the device comprising:

- a hollow rigid housing comprising a distal wall from which there extend side walls whose free ends define a proximal opening;
- a membrane which is situated on the free ends of the side walls to close the proximal opening in substantially hermetic manner, thereby defining a chamber; and
- a duct connected to the rigid body and connecting the chamber to the outside of the injection device;

the membrane being designed during injection to be pierced by a needle for delivering a dose of said substance into the body of the patient via the chamber and the duct; and the side walls and the distal wall of the rigid body being non-pierceable by the needle so as to prevent the needle penetrating into the body of the patient while it is being inserted into the chamber;

the device being characterized in that it further comprises a casing of elastomer material covering the housing and in that the membrane forms an integral portion of the casing, and in that the grade of elastomer used for the membrane is different from that used for the casing.

BRIEF DESCRIPTION OF THE DRAWINGS

Other objects and advantages of the invention will appear more clearly on reading the following description and from the accompanying drawings given purely for illustrative and informative purposes, in which:

FIG. 1 is a diagrammatic perspective view of a first embodiment of an injection device of the invention;

FIGS. 2 and 3 are respectively a plan view and a cross-section view of the FIG. 1 injection device;

FIG. 4 is a cross-section view of the housing and of the duct of the FIG. 1 device;

Figure 5:
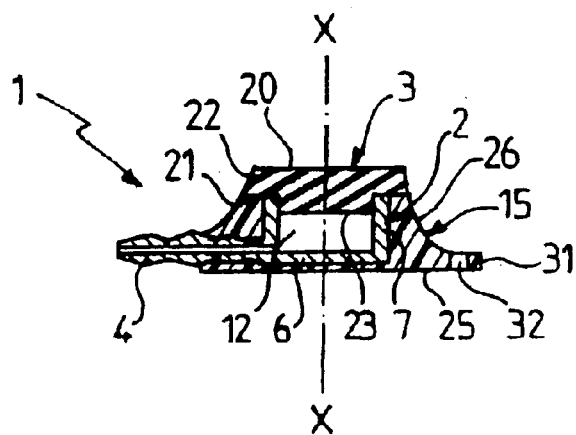
FIG. 5 is a cross-section view through a second embodiment of an injection device of the invention.

In the various figures, elements that are identical or similar are designated by the same references.

BEST METHOD OF PERFORMING THE INVENTION

FIGS. 1 to 4 show a preferred embodiment of an injection device 1 for injecting medical substances in accordance with the invention and designed to be implanted in a subcutaneous zone of the body of a patient in order to inject said substances into the body.

In conventional manner, the device 1 comprises a hollow rigid body 2 which is closed by a membrane 3 and which has a duct 4 connected thereto. The membrane 3 is commonly referred to as a "septum".

The hollow rigid body 2 is formed as a single piece and comprises a distal wall 6 from which there extend side walls 7 whose free ends 8 define a top opening 9. The opening is also referred to as a "proximal" opening insofar as once the device is implanted under the skin of a patient, this opening lies immediately beneath the skin.

Preferably, the distal wall 6 of the housing 2 is in the form of a disk so that the housing comprises a cylinder of circular cross-section about an axis X—X, which cylinder is closed at one of its ends and open at its other end. It is made of a rigid material such as titanium.

The free top ends 8 of the side walls 7 present a certain amount of thickness so as to define a ring 10 which extends parallel to the distal wall 6 of the housing 2.

The height of the side walls 7 of the housing is small compared with the diameter of the distal wall 6, and for example is equal to half the diameter.

The duct 4 is of small diameter and it is fitted to the housing 2. Preferably, the duct is connected to the side walls 7 of the housing in the vicinity of the distal wall 6. It serves to connect the inside volume of the housing 2 to the outside of the injection device 1. The duct 4 is rigid and is likewise made of titanium, for example.

Furthermore, the membrane 3 of the injection device 1 is held in place on the free ends 8 of the side walls 7 of the housing 2 so as to close the proximal opening 9 in substantially hermetic manner. The distal wall 6 and the side walls 7 of the housing 2 thus co-operate with the membrane 3 to define a chamber 12 which is hermetically closed and leakproof.

In conventional manner, the membrane 3 is made of a silicone type elastomer material having "self-healing" properties. These properties mean that after the membrane 3 has been pierced, the pierced hole closes up again automatically so as to ensure that the chamber 12 remains leakproof.

While a dose of medical substance is being injected into the body of the patient, the membrane 3 is designed to have a needle pass therethrough in order to deliver the substance into the body of the patient via the chamber 12 and the duct 4. For this purpose, the duct 4 is connected to a catheter (not shown), in turn mounted so as to open out into the zone of the body where the substance is to be injected.

When the user of the needle, e.g. a nurse, pushes the needle through the membrane 3, the distal wall 6 and the side walls 7 of the housing 2 are strong enough to prevent the needle from leaving the chamber 12, so as to ensure that the end of the needle does not reach the body of the patient and does not give rise to any internal injury within the body of the patient.

According to an important characteristic of the invention, the injection device 1 includes a casing 15 which covers the housing 2 directly. Advantageously, the casing 15 extends over all of the outside faces of the housing 2, i.e. over the bottom face of the distal wall 6 remote from the proximal opening 9, or at least over a fraction of the distal wall 6 corresponding to a peripheral ring on and around the distal wall 6 and over the outside faces of the side walls 7 of the housing. Only the duct 4 projects through the casing 15 to connect the chamber 12 to outside the injection device 1.

By way of example, the casing 15 can be made by molding, by injecting a silicone type elastomer material around the rigid housing 2.

According to the present invention, the membrane 3 constitutes an integral portion of the casing 15. In the meaning of the invention, the term "integral portion" means that the membrane 3 is intimately bonded with the casing 15 insofar as they are made together around the housing 2 during the injection molding process. The membrane 3 and the casing 15 thus form a single piece that can be thought of an overmolding on and around the housing 2. The membrane 3 and the casing 15 are preferably made out of the same type of material, i.e. out of elastomer.

Only the grade of the elastomer used for the casing 15 is or can be different from the grade of the elastomer used for the membrane 3. When the grade of the membrane 3 differs from the grade of the casing 15, it is preferably softer than the casing 15 so that the membrane 3 is less rigid than the casing 15. The resulting injection device 1 is thus of varying hardness. This makes it possible to minimize the trauma to which the body of the patient is subjected, while making it easier for the needle to penetrate through the membrane 3, and this also makes it easier to identify the membrane 3 by touch since it is less rigid than the remainder of the injection device 1 and therefore feels different therefrom.

It will thus be understood that the membrane 3 is not fitted onto the casing 15 and it is not held thereto by positive locking means likewise fitted to the casing. On the contrary, the membrane is intimately bonded to the casing 15 without any plane of separation between them, and together they form a single mass of material with no distinguishable boundary between them. The membrane 3 therefore cannot be separated from the casing 15 and as a result there is no risk of leakage, nor is there any risk of the membrane 3 being expelled.

According to another important characteristic of the invention, the membrane 3 rests on and bears directly against the free ends 8, and it is shaped so as to constitute extra thickness overlying the free ends 8 of the side walls 7 of the housing 2, going away from the distal wall 6 of the housing, thus enabling the membrane to be pierced laterally.

In a preferred variant, the membrane 3 extends over the entire housing 2, from the free ends 8 of the side walls 7. The membrane 3 is thus in the form of a cylinder having the same axis X—X as the housing 2 and possessing a top face 20 and a bottom face 21 between which side walls 22 extend. The height of the side walls 22 is substantially equal to about one-third the height of the injection device 1 as a whole, and is of the order of a few millimeters, for example.

The bottom face 21 bears against the ring 10 defined by the top ends 8 of the side walls 7 of the housing 2. The side walls 22 of the membrane 3 extend in line with the outer side walls of the casing 15.

Thus, during injection, the needle can be inserted into the chamber 12 not only via the top face 20 of the membrane 3, but also through the side faces 22 of the membrane since the membrane is of significant thickness and is directly accessible beneath the skin of the patient. The probability of inserting the needle in a position that is suitable for reaching the chamber 12 is thus increased since the needle can be inserted into the chamber over a wide variety of angles relative to the axis X—X of the housing 2. This makes the nurse's job easier, and minimizes the risk of puncturing the patient without reaching the inside of the chamber 12.

Also advantageously, the casing 15 is of thickness that varies around the housing 2 so as to ensure that the injection device 1 is non-traumatic.

The casing 15 has a base 25 situated close to the distal wall 6 of the housing 2 and of larger diameter than said distal wall 6, with outer side walls 26 extending from the base and converging towards the membrane 3. By way of example, the side walls 26 are frustoconical in shape. This increases the stability of the device 1 inside the patient's body, thereby minimizing any risk of the device turning over.

In order to anchor the device 1 securely inside the patient's body, the base 25 of the casing 15 possesses retention means 30 which, in a first embodiment, are implemented in the form of three lugs 31 projecting from the outline of the base 25. Orifices 32 are formed through the lugs 31. The three lugs 31 are uniformly distributed around the base 25, and are thus mutually spaced apart at 120° intervals.

In a variant, the device 1 is provided with a single lug 31.

The second embodiment as shown in FIG. 5 differs from the first embodiment as described above solely by the thickness of the membrane 3 which in this case is of varying thickness.

The thickness of the membrane 3 in register with the opening 9 of the housing 2 is greater than the thickness of the remainder of the membrane so as to anchor the membrane securely in a transverse direction within the housing 2. The membrane 3 thus comprises a central body 23 which penetrates a short distance into the opening of the housing 2 and co-operating with the remainder of the membrane to form a shoulder. This avoids excessive lateral movement of the membrane 3 while the nurse is palpating the patient's body to locate the device 1 under the patient's skin in order to insert the needle.

Figure 6:
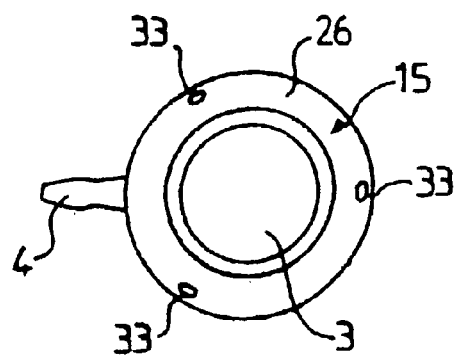
FIGS. 6 and 7 are respectively a plan view and a cross-section view of a third embodiment of an injection device of the present invention.
Figure 7:
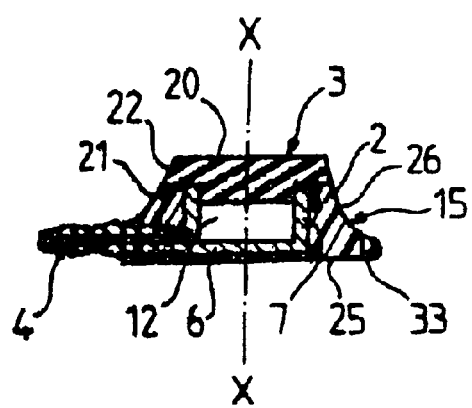

In the third embodiment shown in FIGS. 6 and 7, the retention means 30 of the device 1 are in the form of three orifices 33 which are formed directly through the thickness of the periphery of the base 25.

In this third embodiment, the cross-section of the periphery of the base 25 is rounded so as to be non-traumatic.

Advantageously, the diameter of the base 25 is enlarged to a lesser extent than in the first and second embodiments in order to minimize the risk of leaving any residue of silicone inside the body when the device 1 is removed from the patient.

In yet another variant, an internal chamfer (not shown) is provided on the ring 10 as defined by the free ends 8 of the side walls 7 of the housing 2 so as to make it easier for the needle to penetrate into the chamber 12 when the needle is pushed in from the side, through the side walls 22 of the membrane 3.

The device of the present invention thus possesses a casing 15 which is integral with the membrane 3 and which is of varying flexibility that is adapted as well as possible to ensure that the injection device 1 is not traumatic for the patient's body.

By way of example, this device is particularly suitable for chemotherapy treatment.

SUSCEPTIBILITY OF INDUSTRIAL APPLICATION

The industrial application of the invention lies in making and using on-site devices for injecting medical substances.

What is claimed is:

1. An injection device for injecting medical substances and designed to be implanted in a subcutaneous zone of the body of a patient in order to inject said substances into the body, the device (1) comprising:

a hollow rigid housing (2) comprising a distal wall (6) from which there extend side walls (7) whose free ends (8) define a proximal opening (9);

a membrane (3) which is situated on the free ends (8) of the side walls (7) to close the proximal opening (9) in substantially hermetic manner, thereby defining a chamber (12);

a duct (4) connected to the rigid body (2) and connecting the chamber (12) to the outside of the injection device (1);

the membrane (3) being designed during injection to be pierced by a needle for delivering a dose of said substance into the body of the patient via the chamber (12) and the duct (4);

the side walls (7) and the distal wall (6) of the rigid body (2) being non-pierceable by the needle so as to prevent the needle penetrating into the body of the patient while it is being inserted into the chamber (12); and a casing (15) of elastomer material covering the housing (2), the membrane (3) forming an integral portion of the casing (15), and the grade of elastomer used for the membrane (3) is being different from that used for the casing (15).

2. A device according to claim 1, wherein the grade of elastomer used for the membrane (3) is softer than that used for the casing (15).

3. An injection device according to claim 2, wherein the membrane (3) is shaped to constitute additional thickness extending upwardly from the free ends (8) of the side walls (7) and away from the distal wall (6) of the housing (2) so as to rest on said free ends (8) in such a manner as to be pierceable sideways.

4. An injection device according to claim 3, wherein the membrane (3) extends over the entire housing (2) from the free ends (8) of the side walls (7).

5. A device according to claim 4, wherein the membrane (3) is in the form of a disk with side walls (22) which extend in line with the outer side walls of the casing (15).

6. A device according claim 3, wherein the thickness of the membrane (3) in register with the opening (9) of the housing (2) is greater than the thickness of the remainder of the membrane in order to define a central body (23) provided with a shoulder.

7. An injection device according to claim 1, wherein the casing (15) includes a base (25) of larger size than the distal wall (6) and of a shape that converges from the base (25).

8. An injection device according to claim 7, wherein the periphery of the base (25) is of rounded cross-section.

9. An injection device according to claim 1, wherein the housing (2) is made of titanium, while the casing (15) and the membrane (3) are made of a silicone type elastomer material by being molded around the housing (2).

10. An injection device according to claim 1, wherein the free ends (8) of the side walls (7) are chamfered on the inside.

* * * * *